United States Patent [19]
Darzins et al.

[11] Patent Number: 5,821,088
[45] Date of Patent: Oct. 13, 1998

[54] USE OF GRAM-POSITIVE BACTERIA TO EXPRESS RECOMBINANT PROTEINS

[75] Inventors: Aldis Darzins, Danbury; Stephen Whitehead; Dennis Hruby, both of Redding, all of Conn.; Vincent A. Fischetti, West Hempstead, N.Y.

[73] Assignee: Siga Pharmaceuticals, Inc., New York, N.Y.

[21] Appl. No.: 472,244

[22] Filed: Jun. 7, 1995

Related U.S. Application Data

[63] Continuation-in-part of Ser. No. 735,670, Oct. 17, 1996, which is a continuation of Ser. No. 280,390, Jul. 19, 1994, Pat. No. 5,616,686, which is a continuation of Ser. No. 46,495, Apr. 8, 1993, which is a continuation of Ser. No. 942,432, Sep. 9, 1992, Pat. No. 5,286,058, which is a continuation of Ser. No. 814,323, Dec. 23, 1991, which is a continuation of Ser. No. 742,199, Aug. 5, 1991, which is a continuation of Ser. No. 522,440, May 11, 1990.

[51] Int. Cl.$^6$ ..................................................... C12P 21/04
[52] U.S. Cl. ...................... 435/69.7; 435/69.8; 435/71.2; 435/172.3; 435/219; 435/252.9; 435/253.4; 435/320.1
[58] Field of Search .................................. 435/69.1, 69.7, 435/69.8, 172.1, 172.3, 252.3, 320.1, 71.2, 219, 252.9, 253.4; 536/24.2; 935/22, 23, 27, 29, 47; 530/412

[56] References Cited

U.S. PATENT DOCUMENTS

| | | | |
|---|---|---|---|
| 4,965,197 | 10/1990 | Liebl et al. | 435/69.8 |
| 5,013,653 | 5/1991 | Huston et al. | 435/69.7 |
| 5,115,102 | 5/1992 | Haymore et al. | 530/399 |
| 5,532,142 | 7/1996 | Johnston et al. | 435/69.1 |
| 5,616,686 | 4/1997 | Fischetti et al. | 530/326 |

FOREIGN PATENT DOCUMENTS

| | | |
|---|---|---|
| WO97/08553 | 2/1997 | WIPO . |
| WO97/09437 | 2/1997 | WIPO . |

OTHER PUBLICATIONS

Gianni Pozzi et al., "Delivery and Expression of a Heterologous Antigen on the Surface of Streptococci", *Infection and Immunity* (May 1992) 60:1902–1907.

Gianni Pozzi et al., "Human T–helper cell Recognition of an Immunodominant Epitope of HIV–1 gp120 Expressed on the Surface *Streptococcus gordonii*", *Vaccine* (1994) 12:1071–77.

G. Pozzi, "Expression of M6 Protein Gene of *Streptococcus pyogenes* in *Streptococcus gordonii* After Chromosomal Integration and Transcriptional Fusion" *Infection and Immunity* (1992) 143:449–457.

D. Medaglini et al., "Mucosal and Systemic Immune Responses to a Recombinant Protein Expressed on the Surface of the Oral Commensal Bacterium *Streptococcus gordonii* After Oral Colonization" (1994) *PNAS* (1995) 92:6868–72.

*Primary Examiner*—James Ketter
*Assistant Examiner*—Irem Yucel
*Attorney, Agent, or Firm*—Burns, Doane, Swecker & Mathis, L.L.P.

[57] ABSTRACT

A novel system for cloning and expression of genes in gram-positive bacteria. The expression system is based on the finding that many gram-positive bacteria sort proteins to their cell surface through cis-acting N-terminal signal sequences and C-terminal anchor regions. In particular, the cell sorting signals of the streptococcal M6 protein, a well-known surface molecule, are used to construct a gram-positive expression system, designated SPEX (Streptococcal Protein Expression). Expression is achieved by cloning the gene of interest into an appropriate SPEX cassette which is then stably introduced into a bacterial host, such as the human commensal *Streptococcus gordonii*. Depending on the SPEX vector used, recombinant proteins can be anchored to the cell wall prior to release by specific endoproteolytic cleavage or secreted into the culture medium during bacterial growth. The use of host bacteria lacking extracellular proteases should protect secreted proteins from proteolytic degradation. Several expression vectors in this system also produce specifically-tagged recombinant proteins which allows for a one-step purification of the resulting product.

45 Claims, 9 Drawing Sheets

FIG. 1

| | | | |
|---|---|---|---|
| ADANKAQA | LPETGE | ENPLIGTTVFGGLSLALGAALLAG | RRREL | Protein A |
| PMKETKRQ | LPETGE | TANPFFTAAAALTVMATAGVAAVV | KRKEEN | M6 |
| TKQKAKFV | LPSTGE | QAGLLLTTVGLVIVAVAGVYFY | RTRR | WapA |
| AMTQQKRT | LPSTGE | TANPFFTAAAATVMVSAGMLAL | KRKEEN | M49 |
| PMAQTKRQ | LPSTGE | ETTNPFFTA........ | | IgA-BP |
| DDAKKAET | LPTTGE | GSNPFFTAAALAVMAGAGALAVA | KRKEEN | Protein G |
| KPQSKKSE | LPETGG | EESTNKGMLFGGLFSILGLALL | RRNKKNHKA | Fn-BP |
| IPNTKLGE | LPSTGS | IGTYLFKAIGSAAMIGAIGIYIV | KRRKA | T6 |
| QPSSVQET | LPNTGV | TNNAYMPLLGIIGLVTSFSLLGL | KAKKD | Pac |
| QLTSGKGA | LPKTGE | TTERPAFGFLGVIVVILMGVLGL | KRKQREE | Wg2 |

FIG. 3A

```
CCT TAC CTT TTG GCT TTT ATT ATT TAC AAT ACA ATT ATT AGA GTT AAA CCCTGA AAA TGAGGG TTT TTC CTA AAA         75
AAT GAT AAC A┌TA AGGAGC┐ATA AAA ATG GCT AAA AAT AACACG AAT AGA CACTAT TCG CTT AGA AAA TTA AAA AAA        150
        RBS                   M   A   K   N   N   T   N   R   H   Y   S   L   R   K   L   K   K
                             -42
GGT ACT GCA TCA GTA GCA GTG GCT TTG AGT GTA ATAGGGGCAGGA TTA GTTGTC AAT ACT AAT GAA GTT AGT GCA          225
 G   T   A   S   V   A   V   A   L   S   V   I   G   A   G   L   V   V   N   T   N   E   V   S   A
    Avrll                                                                                       -1
AGA GTG TTT CCT AGGGGGACG GTA GAA AAC CCGGAC AAA GCA CGA GAA CTT CTT AAC AAG TAT GAC GTA GAG AAC        300
 R   V   F   P   R   G   T   V   E   N   P   D   K   A   R   E   L   L   N   K   Y   D   V   E   N
+1                                                                       +16
TCT ATG TTA CAA GCT AAT AAT GACAAG TTA ACA GAT CAG AAT AAA AAC TTA ACA GAT CAG AAT AAA AAC TTA ACA      375
 S   M   L   Q   A   N   N   D   K   L   T   D   Q   N   K   N   L   T   D   Q   N   K   N   L   T
ACT GAG AAT AAA AAC TTA ACA ACT GAG AAT AAG GAG TTA AAA GCT GAG GAG AAT AGG TTA ACA CTT GAG AAT AAA     450
 T   E   N   K   N   L   T   T   E   N   K   E   L   K   A   E   E   N   R   L   T   T   E   N   K
AAC TTA ACA ACT GAG AAT AAG GAG TTA AAA GCT GAG GAG AAT AGG TTA ACA CTT GAG AAT AAA GGG TTA ACT AAA     525
 N   L   T   T   E   N   K   E   L   K   A   E   E   N   R   L   T   T   E   N   K   G   L   T   K
                                                                                       Kpnl
AAG TTA AGT GAA GCT GAA GAA GAA GCA GCA AAT AAA GAG GAG CAA GAA AGT AAA GAA GCC ATT GGT ACC CTT AAA AAA 600
 K   L   S   E   A   E   E   E   A   A   N   K   E   R   E   N   K   E   A   I   G   T   L   K   K
ACC TTG GAT GAG ACA GTA AAA GAT AAA ATT GCT AAG GAG CAA GAA AGT AAA GAA ACC ATT GGT ACC CTT AAA AAA     AAA
 T   L   D   E   T   V   K   D   K   I   A   K   E   Q   E   S   K   E   T   I   G   T   L   K   K
ACC TTG GAT GAG ACA GTA AAA GAT AAA ATT GCT AAG GAG CAA GAA AGT AAA GAA ACC ATT GGT ACC CTT AAA AAA     750
 T   L   D   E   T   V   K   D   K   I   A   K   E   Q   E   S   K   E   T   I   G   T   L   K   K
ACC TTG GAT GAG ACA GTA AAA GAT AAA ATT GCT AAG GAG CAA GAA AGT AAA GAA ACC ATT GGT ACC CTT AAA AAA     825
 T   L   D   E   T   V   K   D   K   I   A   K   E   Q   E   S   K   E   T   I   G   T   L   K   K
```

FIG. 3B

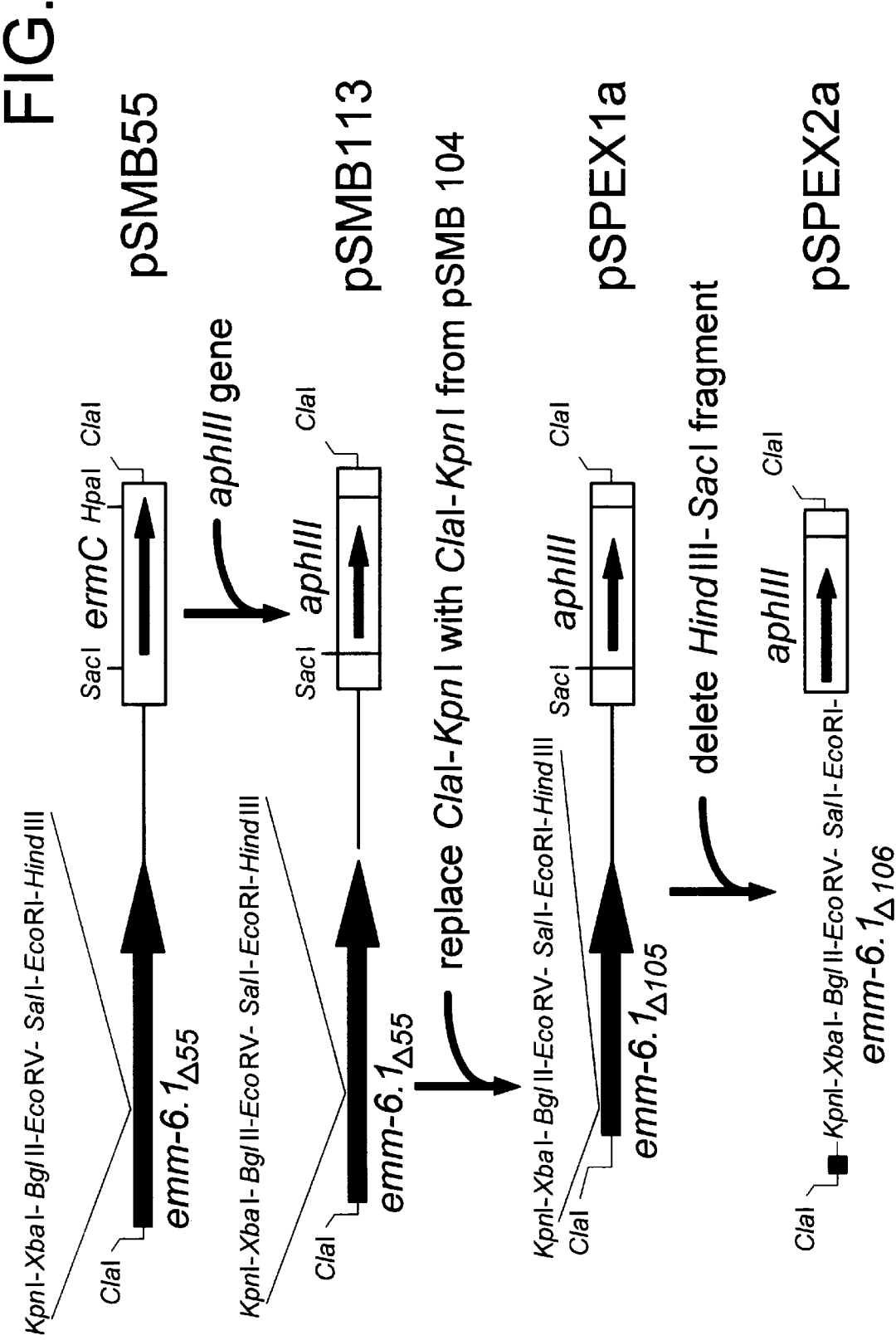

USE OF GRAM-POSITIVE BACTERIA TO EXPRESS RECOMBINANT PROTEINS

This application is a continuation-in-part of application Ser. No. 08/735,670, filed Oct. 17, 1996, which is a continuation of application Ser. No. 08/280,390, filed Jul. 26, 1994, Pat. No. 5,616,686, which is a continuation of application Ser. No. 08/046,495, filed Apr. 8, 1993 (abandoned), which is a continuation of application Ser. No. 07/942,432, filed Jun. 18, 1992 (abandoned), which is a continuation of application Ser. No. 07/814,323, filed Dec. 23, 1992 (abandoned), which is a continuation of application Ser. No. 07/742,199, filed Aug. 5, 1991 (abandoned), which is a continuation of application Ser. No. 07/522,440, filed May 11, 1990 (abandoned).

BACKGROUND OF THE INVENTION

1. Field of the Invention

The present invention relates to the construction and use of a novel gram-positive expression vector system. Protein fusions containing the amino and carboxy sorting sequences of a gram-positive surface polypeptide can be anchored to the surface of a heterologous host. Alternatively, recombinant proteins may be secreted into the growth medium. This system can be used for overproducing and purifying recombinant proteins or peptides for any purpose, including but not limited to commercial scale production of diagnostic and vaccine antigens and therapeutic proteins, such as hormones and growth factors.

2. Description of the Related Art

The ability to overproduce many prokaryotic and eukaryotic proteins has been made possible through the use of recombinant DNA technology. The introduction of chimeric DNA molecules into *Escherichia coli* has been the method of choice to express a variety of gene products. The main impetus behind the use of *E. coli*-based protein production systems is the host's short generation time and well-developed genetics. Yet despite the development of many efficient *E. coli*-based gene expression systems in recent years, the most important concern continues to be that associated with downstream processing of the product. Recombinant proteins produced in *E. coli* do not readily cross the outer cell membrane (OM); as a result, polypeptides must be purified from the cytoplasm or periplasmic space (PS). Purification of proteins from these cellular compartments can be somewhat difficult. Frequently encountered problems include low product yields, contamination with potentially toxic cellular material (i.e., endotoxin) and the formation of large amounts of partially folded polypeptide chains in non-active aggregates, called inclusion bodies. As a result of these inherent purification difficulties, a great deal of attention has recently been focused on the natural ability of many gram-positive bacteria to export proteins beyond their cell wall boundaries. In spite of the fact that the genetics of gram-positive bacteria are not as well-elucidated as those of *E. coli*, these microorganisms have, nevertheless, become recognized as more favorable candidates as hosts for the production of recombinant proteins.

Proteins exported across the gram-positive cytoplasmic membrane (CM) generally have two fates: they are either released (secreted) into the extracellular milieu or they remain anchored to the cell wall/membrane. Many of the recently developed gram-positive based expression systems have relied exclusively on the former route of protein export (i.e., secretion). The basic strategy for directing the secretion of proteins in gram-positive expression systems involves fusing target proteins with functional N-terminal signal sequences of the gram-positive secretion systems currently available. By far, the most popular hosts belong to the genus Bacillus. This group of microorganisms has been used by industry for the production of a variety of economically important proteins (Priest, *Bacteriol. Rev.*, 41:711 (1977); Glenn, Ann. *Rev. Microbiol.*, 30:41 (1976)). Perhaps the most extensively studied gram-positive host-vector expression system is based on the *B. amyloliquefaciens* alpha-amylase gene (Ulmanen et al., *J. Bacteriol.*, 162:176 (1985); Palva et al., *Proc. Natl. Acad. Sci. U.S.A.*, 79:5582 (1982); Palva et al., *Gene*, 22:229 (1983); Lundstrom et al., *Virus Res.*, 2:69 (1985)). However, expression systems based on other gram-positive hosts such as *B. subtilis, B. coagulans, B. licheniformis* (U.S. Pat. Nos. 4,824,782, 5,171,673, 4,711,843; WO patent 8,605,812; Chang, S., Methods in Enzymology, 153:507–516 (1987)), *Lactococcus and Lactobacillus spp.* (U.S. Pat. No. 5,242,821), *Staphylococcus spp.* (Abrahmsen et al., *EMBO J.* 4:3901–3906 (1986)), *Streptomyces spp.* (U.S. Pat. No. 4,745,056; JP Patent 2,002,379; EP 352,707) and *Corynebacterium spp.* (U.S. Pat. No. 4,965,197; WO Patent 9,303,158) have also been developed for general use.

Gram-positive secretion systems provide several advantages over traditional *E. coli* based expression systems. One obvious benefit is that proteins exported beyond the cell wall usually retain their native conformation. As a result, one can take full advantage of established purification protocols which are based on the functional properties of the active protein. In addition, gram-positive expression systems usually generate higher protein yields which are generally free of potentially toxic contaminating cellular material.

There are, however, several practical limitations to the purification of extracellular proteins. The first concern is that of protein instability. Recombinant proteins secreted by many gram-positive hosts are extremely sensitive to proteolytic degradation by host-encoded extracellular proteases. The presence of such proteases can drastically affect protein yield. Fortunately, significant improvements have been achieved in maintaining the viability of secreted proteins by genetically modifying host strains with reduced extracellular protease activities (Kawamura et al., *J. Bacteriol.*, 160:442 (1984); U.S. Pat. No. 5,084,383).

Another important point to consider when using gram-positive secretion systems is the requirement for extensive downstream processing. It is widely accepted that the purification of recombinant proteins from bulky, large volume fermentations is an extremely time consuming and costly proposition, both in terms of equipment and manpower. In those cases where the use of a gram-positive secretion system is simply not practical, it is common to resort to a less expensive, gram-negative based expression system. The decision to use *E. Coli* as an alternative expression host, despite the potential pitfalls, is made simply on the basis that recombinant polypeptides remain associated with the bacterial cell (i.e., intracellular or periplasmic) and hence are generally easier to purify. Therefore, it is clear that what is needed in this art is a bacterial expression system that incorporates the salient features of both gram-positive (i.e., protein secretion) and gram-negative (i.e., protein compartmentalization) systems. A novel, but simple alternative to the currently available bacterial expression systems would be the development of a gram-positive system that is able to specifically anchor or attach recombinant proteins directly to the cell wall surface. In this way the anchoring process can become an integral part of the purification process. For example, cells harboring a recombinant protein attached to the cell surface would be washed, collected, resuspended in a small volume and then treated with a specific agent to affect the release of the desired protein. Following removal of the bacterial cells, the resulting supernatant fluid would be highly enriched for the protein product.

The cell wall of gram-positive bacteria is a complex organelle, which is assembled from peptidoglycans, carbohydrates, and proteins with different biological properties. Surface proteins differ from naturally secreted products in that the former require specific sorting signals that presumably allow them to deviate from the normal default pathway of protein export. Despite the fact that many of the biologically important gram-positive proteins, including the streptococcal M protein, and the protein A and fibronectin binding proteins of *S. aureus*, are anchored at the cell surface, the cell wall of gram-positive bacteria remains a relatively unknown cellular compartment.

While the normal N-terminal export signals that serve as the basis for bacterial secretion systems have been extensively characterized (Abrahmsen et al., *EMBO J.*, 4:3901–3906 (1985); Heijne and Abrahmsen, *FEBS Letters*, 244:439–446 (1989); Pugsley, *Microbio. Reviews*, 57:50–108 (1993)), the cis-acting sorting signals that orchestrate the anchoring of cellular proteins to the gram-positive cell wall have been only recently elucidated. Sequence alignment of well over 50 gram-positive surface proteins to date (excluding those from *B. subtilis* and *S. pneumoniae*) has revealed the existence of both amino- and carboxy-terminal secretion/anchoring signals. As expected, all of the proteins examined contain an N-terminal signal sequence that presumably directs them to the cellular export machinery. The C-termini of these proteins contain a predominantly hydrophobic, potential membrane spanning region that is immediately followed by a charged tail (Fischetti et al., *Mol. Microbiol.*, 4:1603–1605; FIG. 1: Darkly shaded region=LP(X)TG(X) consensus sequence; lightly shaded region=carboxy-terminal hydrophobic, potential membrane spanning region; residues in bold= charged protein tail; Protein A=*Staphylococcus aureus* protein A; M6=*Streptococcus pyogenes* M6 protein; WapA=*S. mutans* wall-associated protein A; M49=*S. pyogenes* M49 protein; IgA-BP=streptococcal IgA-binding protein; Protein G=streptococcal protein G; Fn-BP=staphylococcal fibronectin-binding protein; T6=streptococcal T6 protein; Pac=*S. mutans* surface protein; Wg2=*S. cremoris* surface protease). Preceding the hydrophobic domain is a proline/glycine-rich region which has been predicted to span the peptidoglycan cell wall in a beta-sheet-like conformation. Within this region, all of the surface proteins examined have a nearly 100% conserved hexapeptide with the consensus LP(X)TG(X), where X is usually a Thr or Ser and sometimes a Gly, Lys, or Asn (FIG. 1). The conservation of the C-terminal sequence elements (i.e., LP(X)TG(X) motif, hydrophobic membrane spanning region and charged tail) suggests that the process of sorting and anchoring polypeptides to the bacterial cell wall is shared by many gram-positive species (Fischetti et al., *Mol. Microbiol.*, 4:1603–1605 (1990); Fischetti et al., *Curr. Opinion Biotechnol.*, 4:603–610 (1993)).

The functional importance of the carboxy-terminal sorting elements identified by sequence alignment analysis has been confirmed using protein A (Moks et al., *Eur. J. Biochem.*, 156:637–643 (1986)), a well-characterized surface protein of *S. aureus*, as a model system. Protein A, a single polypeptide chain, contains two major functional domains. The N-terminal domain contains a 36 amino acid signal peptide sequence followed by several repeated sequence modules (E, D, A, B, and C) that have immunoglobulin binding activity. The C-terminal domain contains conserved sorting signals which are thought to be responsible for anchoring protein A to the cell wall (Guss et al., *Eur. J. Biochem.*, 138:413–420(1984); Guss et al., *Eur. J. Biochem.*, 143:685 (1984); Fischetti et al., *Mol. Microbiol.*, 4:1603–160S (1990)). Using deletion analysis, Schneewind et al. (*Cell*, 70:267–281 (1992)) confirmed that the proper sorting of protein A in *S. aureus* requires all three of the conserved sequence elements (i.e., —LPETGE-motif, C-terminal hydrophobic domain, and charged tail). Based on their results, Schneewind et al. (*Cell*, 70:267–281 (1992)) have proposed the following sequence of events in the anchoring of protein A and presumably many other gram-positive proteins to the cell surface. First, the N-terminal signal sequence of protein A directs the polypeptide into the general secretion pathway (GSP) (for reviews, see Pugsley, *Microbio. Reviews*, 57:50–108 (1993); Salmond and Reeves, *TIBS* 18:7–12 (1993)). During the process of membrane translocation, the main function of the C-terminal charged tail is to prevent secretion of the protein into the medium. Translocation of protein A across the membrane presumably results in the recognition of the C-terminal sorting signal. Following recognition, the LPETGE (LPXTGX) motif is cleaved specifically between the threonine (T) and glycine (G) residues and the resulting N-terminal protein fragment is then covalently linked to the *S. aureus* cell wall (Navarre and Schneewind, *Mol. Microbiol.*, 14:115–121 (1994)).

Because the anchor motif of gram-positive surface proteins is conserved among a wide variety of molecules and several different gram-positive species, a logical question to ask is whether it would be possible to anchor a well-known surface protein to the cell wall of a heterologous gram-positive host. Pozzi et al. (*Res. Microbiol.*, 143:449–457 (1992)), using the fibrillar streptococcal M protein, were the first to address the question of protein anchoring in heterologous gram-positive hosts. Structurally, the M protein consists of an extended central alpha-helical coiled-coil rod flanked by functional end domains (FIG. 2) (Phillips et al., *Proc. Natl. Acad. Sci.* (*USA*), 78:4689–4693 (1981); Fischetti, *Clin. Microbiol. Reviews*, 2:285–314 (1989))(FIG. 2, (A) Structural representation of the M6 protein; (B) Linear representation of the M6 protein molecule. The map displays the N-terminal signal peptide (S), several repeated domains (A, B, C, and D), the proline/glycine rich region that contains the LPSTGE motif (LPXTGX), the C-terminal hydrophobic, potential membrane spanning domain (black bar), and charged tail (KRKEEN). Amino and carboxy terminal residues important for export and cell wall sorting/anchoring of the M6 protein are shaded. The anchor region is not drawn to scale.). The N-terminus contains a 42-residue signal sequence required for proper processing (Fischetti, *Clin. Microbiol. Reviews*, 2:285–314 (1989); Hollingshead et al., *J. Biol. Chem.*, 261:1677–1686 (1986)), while the C-terminus, as determined by sequence comparisons, contains the conserved residues that are necessary for cell sorting and anchoring (Fischetti et al., *Mol. Microbiol.*, 4:1603–1605 (1990); Pancholi and Fischetti, *J. Bacteriol.*, 170:2618–2624 (1988); FIG. 1). After integration of a promoterless emm-6.1 gene in the chromosome of the human oral commensal *S. gordonii*, it was demonstrated that the M6 protein was correctly localized to the cell wall of the heterologous host (Pozzi et al., *Res. Microbiol.*, 143:449–457 (1992)).

The next logical step was to examine the possibility of exploiting the M6 sorting signals in order to express recombinant proteins on the surface of a gram-positive host. The M6 protein has been successfully modified to deliver several heterologous antigens, such as sequences derived from the human papilloma virus type 16 E7 protein, the immunodominant epitope of HIV-1 gp120 and the major allergen of white-face hornet venom, to the surface of *S. gordonii* (Pozzi et al., *Infect. Immun.*, 60:1902–1907 (1992); Pozzi et al., *Vaccine*, 12:1071–1077 (1994); Medaglini et al., *Proc. Natl. Acad. Sci. (USA)*, in press (1995)). Gram-positive oral commensal bacteria expressing recombinant fusion proteins on their cell surface have been used to elicit both a mucosal and systemic immune response to foreign antigens while colonizing the oropharynx (Fischetti et al., *Curr. Opinion Biotechnol.*, 4:603–610 (1993); Medaglini et al., *Proc. Natl. Acad. Sci. (USA)*, in press (1995)).

The recent results of the M6 experiments are important for two main reasons. First, they serve to confirm the hypothesis that the mechanism of protein sorting and anchoring is an extremely well conserved, if not universal, process in gram-positive bacteria. More importantly, these experiments are evidence for proof of the concept that it is possible to exploit cell wall protein sorting signals for the purpose of constructing novel expression systems that anchor recombinant proteins to the surface of a gram-positive bacterial host. Therefore, in view of the aforementioned deficiencies attendant with prior art expression systems, it should be apparent that there still exists a need in the art for the construction and use of a unique gram-positive protein expression system.

SUMMARY OF THE INVENTION

Accordingly, a major objective of the present invention is to develop a gram-positive bacterial expression system that can be used for the production and purification of recombinant proteins.

It is also the objective of this invention to provide, as a specific example, the construction and use of the SPEX system (for Streptococcal protein expression), which is based on the streptococcal M6 protein. This system will allow one familiar in the art of genetic manipulation and protein biochemistry to express and purify recombinant proteins from gram-positive hosts, such as the human oral commensal *S. gordonii*.

More specifically, the present invention provides a method for expressing proteins in gram-positive bacteria, comprising selecting a heterologous bacterial host which is gram-positive, deficient in extracellular protease production, and capable of anchoring surface proteins via C-terminal sorting signals; introducing into the host a plasmid vector comprising DNA fragments encoding amino and carboxy terminal sorting sequences of a gram-positive cell wall surface protein, DNA fragments coding for the desired protein product, and transcriptional and translational control sequences that function in the chosen host; expressing a fusion protein comprising the desired protein product, an N-terminal signal sequence, and a C-terminal sorting sequence wherein the expressed protein is anchored to the host's cell surface; cleaving the anchored protein from the host's cell surface using a protease; and purifying the cleaved protein from the supernatant fluid. The present invention also provides an alternative method for expressing proteins in a gram-positive host whereby the desired protein product is secreted into the extracellular space, and for purifying the secreted proteins from the supernatant fluid.

Briefly, the present invention features general methods for the construction and use of a gram-positive host/vector system that uses the cell sorting signals of surface proteins for targeted attachment to the cell wall. To demonstrate the utility of this system, the invention also describes the construction of several specialized vectors, designated SPEX, which are based on the *S. pyogenes* M6 protein. These vectors are intended to be used for the expression of proteins and peptides in gram-positive bacteria such as the human oral commensal, *S. gordonii*. A variety of recombinant protein products can be expressed by selecting the appropriate SPEX cloning vector. Several protein configurations are possible such as the presence of a combination of polyhistidine tag and protein A IgG binding domains, factor Xa or TEV protease cleavage sites, and a cell wall anchoring domain LP(X)TG(X). Each of the cloning vectors acts as a shuttle plasmid which permits the initial cloning to be performed in *E. coli*, followed by transformation into a gram-positive host, such as the naturally competent *S. gordonii* V288 (Challis). Depending on the SPEX vector used, recombinant proteins can be purified from an anchored state after cleavage with a specific protease or, alternatively, from the culture medium.

With the foregoing and other objectives, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 1 depicts the alignment of the C-terminal residues from a select group of gram-positive surface proteins.

FIG. 3 depicts the nucleotide sequence of the *S. pyogenes* emm6 gene and adjacent DNA regions.

FIG. 4 is a diagrammatic representation of the construction of SPEX vectors. The pBLUESCRIPT (Ap$^r$) backbone of each plasmid is not shown.

DETAILED DESCRIPTION OF THE PREFERRED EMBODIMENTS OF THE INVENTION

Figure 2A:
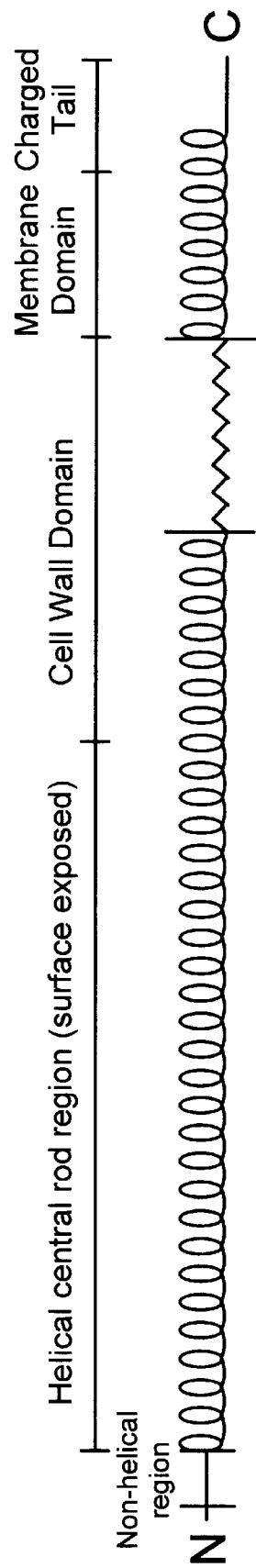
FIGS. 2A and 2B depicts the functional domains of the *S. pyogenes* M6 protein.
Figure 2B:
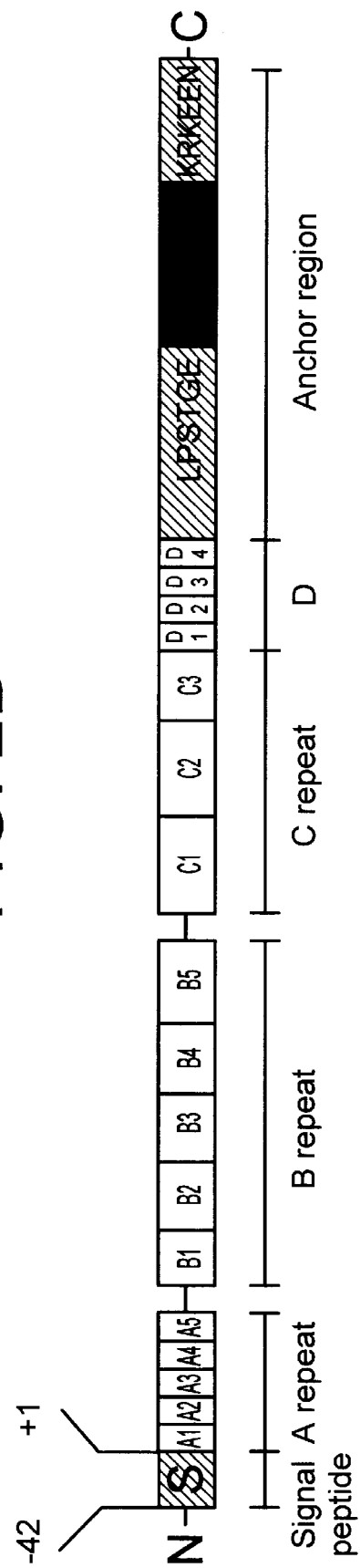

More particularly, the present invention relates to general methods for the construction and use of a novel gram-positive expression system. Proteins produced by the expression system described herein can be purified either directly from the cell surface or from the supernatant fluid following secretion. For example, an expression system based on the well-known M6 protein of *S. pyogenes* is also described. This expression system, designated SPEX (for Streptococcal protein expression), uses the human oral commensal *Streptococcus gordonii* as a model host for this group of organisms.

A. General Method

The first major factor to be considered when constructing the gram-positive expression system is to determine which bacterium to use as a host. To be effective in the present invention the bacterial host should be a gram-positive bacteria that is capable of anchoring surface proteins via C-terminal sorting signals. Such gram-positive bacteria include, but are not limited to, the genera *Aerococcus, Bifidobacterium, Corprococcus, Deinobacter, Deinococcus, Enterococcus, Gemella, Lactobacillus, Lactococcus, Leuconostoc, Marinococcus, Melissococcus, Micrococcus, Pediococcus, Peptococcus, Peptostreptococcus, Planococcus, Ruminococcus, Saccharococcus, Salinococcus, Carcina, Staphylococcus, Stomatococcus, Streptococcus, Trichococcus*, and *Vagococcus*. To gain the maximum benefit from the present invention, the bacterial host should be deficient in extracellular protease production.

In the present invention the more preferred species to be used as an expression host is *Streptococcus gordonii*. The most preferred strain is a protease deficient variant of V288 (Challis).

The second major consideration is the selection of the gram-positive cell wall protein to be used as the basis for the construction of the expression vectors. Nearly all surface molecules of gram-positive bacteria have amino and carboxy terminal sorting signals that specifically target them for cell wall attachment (Fischetti et al., *Mol. Microbiol.*, 4:1603–1605 (1990)). The expression system used in the practice of the present invention can be constructed with any gram-positive surface protein that contains the appropriate sorting signals. Such sorting signals can be readily identified by those skilled in the art. Sources of surface proteins include, but are not limited to, such gram-positive genera as *Aerococcus, Bifidobacterium, Corprococcus, Deinobacter, Deinococcus, Enterococcus, Gemella, Lactobacillus, Lactococcus, Leuconostoc, Marinococcus, Melissococcus, Micrococcus, Pediococcus, Peptococcus, Peptostreptococcus, Planococcus, Ruminococcus, Saccharococcus, Salinococcus, Carcina, Staphylococcus, Stomatococcus, Streptococcus, Trichococcus*, and *Vagococcus*.

Figure 3B:
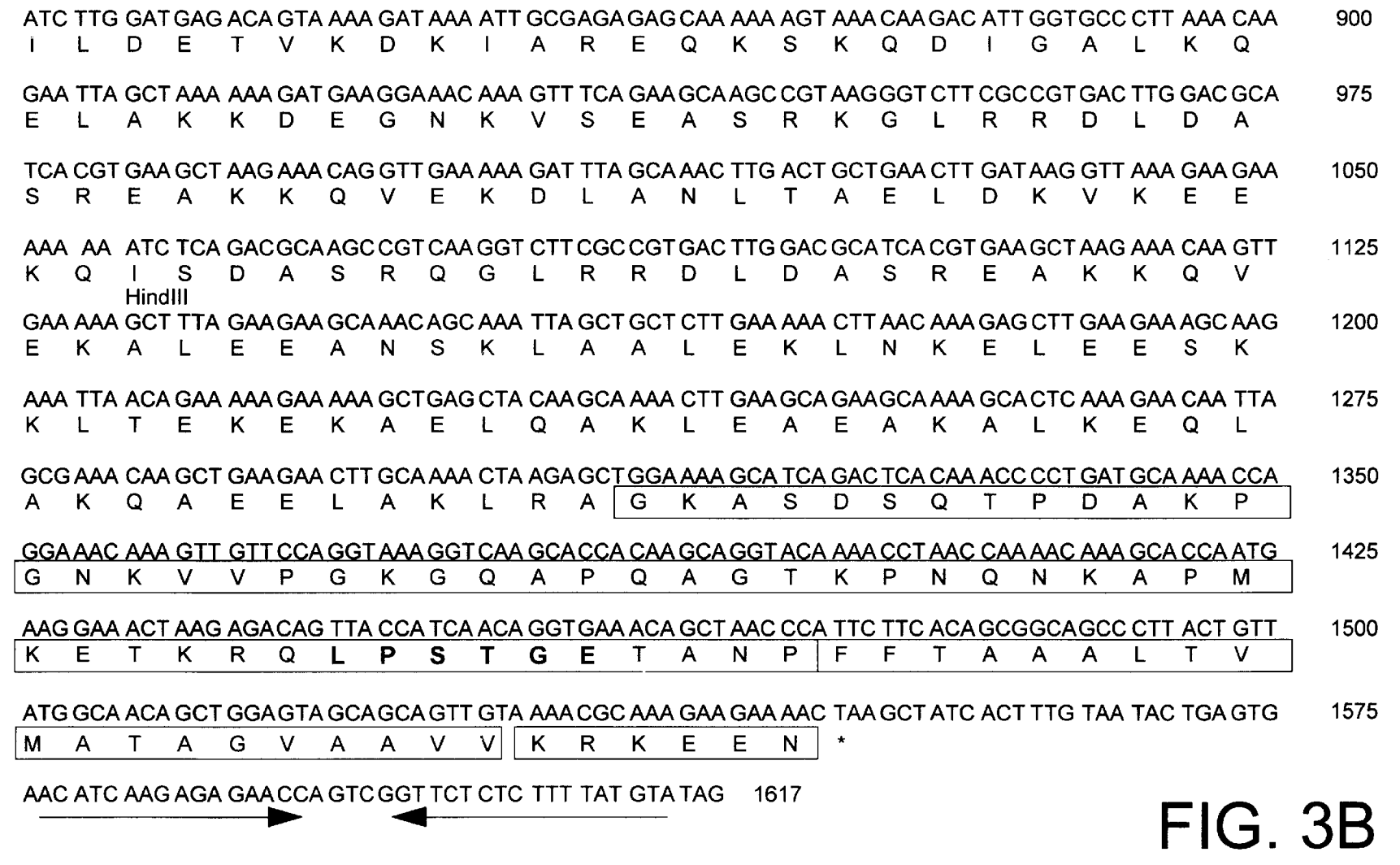

The more preferred protein to be used in the present invention is the type-6M protein of *Streptococcus pyogenes*. The structural gene for the type 6-M protein from *S. pyogenes* has been cloned (Scott and Fischetti, *Science*, 221:758–760 (1983)) and the complete nucleotide sequence has been determined (Hollingshead et al., *J. Biol. Chem.* 261:1677–1686 (1986)). This sequence is shown in FIG. 3. The predicted M6 amino acid residues are shown below the DNA sequence. The putative ribosome binding site (RBS) is boxed and the signal peptide (−42 to −1) is underlined. The mature polypeptide represents residues +1 to 441. The proline/glycine rich cell wall domain is shown as unshaded rectangles. The LPXTGX (LPSTGE) motif is shown in bold letters. The adjacent lightly shaded rectangle represents the hydrophobic, membrane spanning domain and the darkly shaded rectangle represents the C-terminal charged tail. Relevant restriction sites are shown above the DNA sequence. A transcriptional terminator is shown as the inverted repeat structure denoted by the arrows.

The next consideration is to isolate and characterize the DNA sequence that codes for the cell wall protein in the chosen host. Methods used for the construction and screening of genomic libraries (i.e., plasmid, cosmid, phage or YAC) to isolate the appropriate protein coding sequence and techniques for determining its nucleotide sequence are known to those skilled in the art of genetic engineering. See, e.g., Sambrook, Fritsch & Maniatis, *Molecular Cloning: A Laboratory Manual.*, Second Edition (1989); Maniatis, Fritsch, & Sambrook, *Molecular Cloning: A Laboratory Manual* (1982) and Griffin & Griffin, *PCR Technology: Current Innovations* (1994).

The DNA fragments that encode the amino and carboxy terminal sorting signals of the surface protein can be isolated using recombinant DNA techniques familiar to those skilled in the art. These fragments can be assembled on an *E. coli* cloning vector such as pUC18/19 or any other appropriate plasmid element. The N-terminal signal should include a complete leader sequence as well as a number of amino acid residues from the N-terminus of the mature protein. The inclusion of these sequences will insure proper targeting to the cellular export machinery and correct processing during the actual translocation process. The C-terminal sorting (i.e., anchor) signals should include the LPXTGX motif (where X is any amino acid residue), a hydrophobic membrane spanning domain and a charged tail. A comparison of such sorting sequences is shown in FIG. 1. The darkly shaded sequences on the left side of the alignment represents the LP(X)TG(X) consensus sequence and the proteins were aligned from this sequence. The lightly shaded region on the right side of the alignment represents the carboxyl-terminal hydrophobic, potential membrane spanning region. Residues shown in bold represent the charged protein tail.

To facilitate the construction of heterologous fusion proteins, a small DNA fragment containing the recognition sequences for several restriction endonucleases can be placed between the DNA sequences that encode the amino and carboxy terminal sorting signals. This multiple cloning site (MCS) will facilitate the insertion of heterologous protein coding sequences and upon expression will generate in-frame protein fusions that are anchored to the gram-positive cell wall surface. Alternatively, expression vectors can also be constructed that lack the C-terminal anchor signals. In this case, the protein fusions will not be targeted for anchoring but, instead, will be secreted into the extracellular space.

Figure 5:
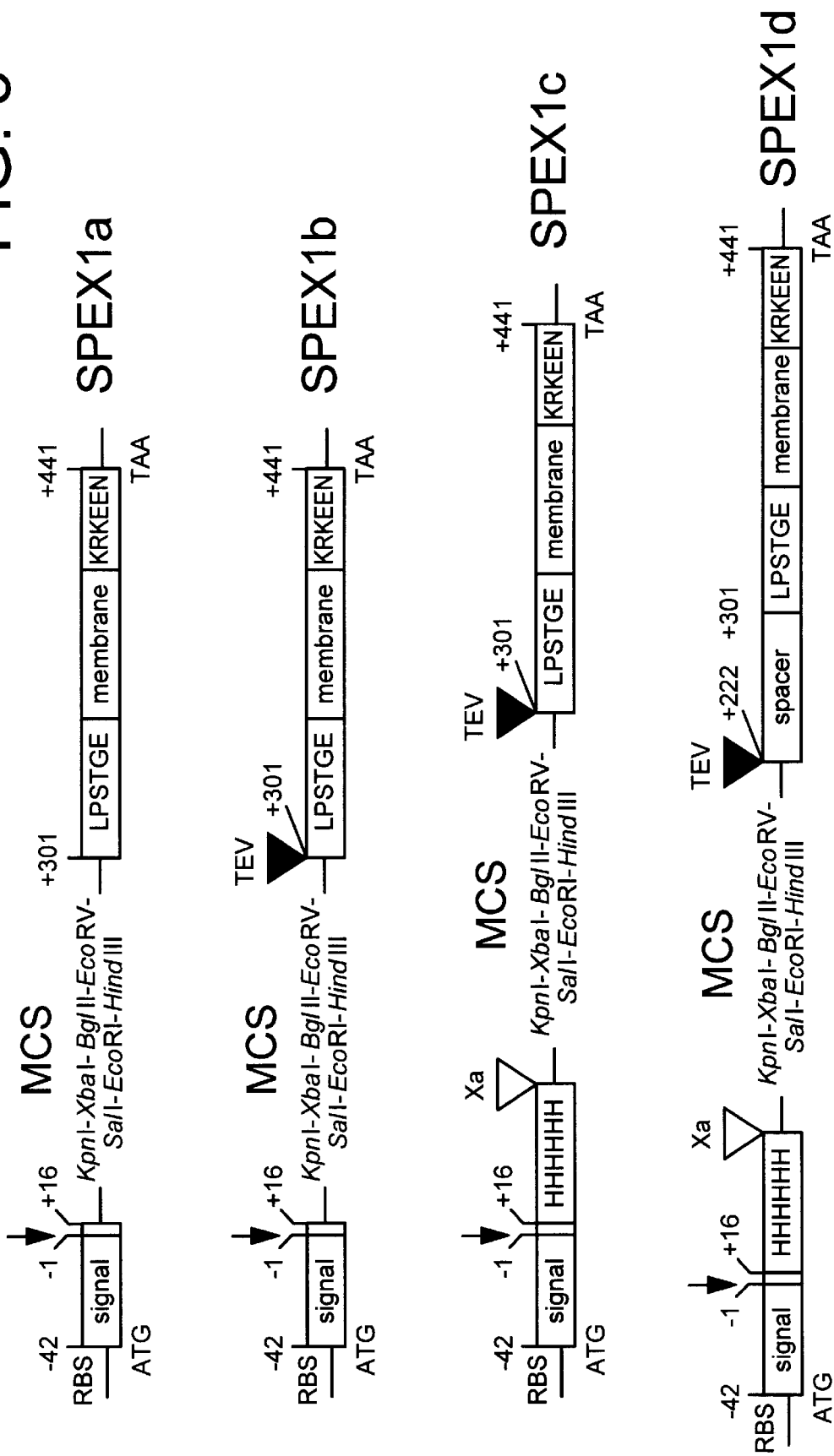
FIG. 5 illustrates possible SPEX cassettes useful for anchored surface production and purification of recombinant proteins.

The vectors described in the present invention will allow one familiar in the art to produce recombinant proteins that are either anchored at the cell surface or secreted into the extracellular space. Regardless of the final destination of the target protein, all of the vectors contain the M6 ribosome binding site (RBS), translation initiation codon (ATG) and the 42 amino acid leader sequence (−42 to −1) (FIG. 3, 4 and 5). In addition, all of the vectors contain some portion of the mature N-terminus of the M6 protein. Previous studies have demonstrated that as many as 122 amino acids of the mature M protein N-terminus are also required for successful translocation. However, more recently, it has been shown that as few as 5 N-terminal amino acid residues of the mature protein may be required for proper processing and translocation of a M6 fusion protein to the cell surface (Fischetti et al., *Curr. Opinion Biotechnol.* 4:603–610 (1993)). The preferred number of M6 amino terminal residues to be used in the practice of the present invention is 58 and include residues −42 to +16 (FIG. 3).

The preferred C-terminal sorting signals used in the present invention are also derived from the M protein of type-6 *S. pyogenes*. The vectors designed for targeted protein anchoring contain the M6 C-terminal residues 302 to 441, termination codon (TAA) and downstream sequences, which include a putative transcriptional terminator (FIG. 3). Vectors that are designed for protein secretion do not contain the M6 C-terminal sorting signals.

The expression vector systems of the present invention are suitable for overproducing and purifying any desired protein. At the very least, the expression vector systems of the present invention are useful for overproducing and purifying recombinant proteins or peptides. These proteins or peptides may be used for any purpose; for example, they may be used to generate diagnostic and vaccine antigens and therapeutic proteins, such as hormones and growth factors, and the like.

To facilitate the release of anchored fusion proteins from the gram-positive cell wall, cleavage sites for various proteolytic enzymes can be engineered into the expression vectors. These unique sequences can optionally be incorporated into the vectors so that they reside either immediately downstream of the N-terminal signal peptide or immediately upstream of the C-terminal sorting signal domain. It is also possible to engineer cleavage sites at both locations. Proteases that may be suitable include, but are not limited to, the proteinase of tobacco etch virus (TEV), thrombin, enterokinase, and factor Xa.

A variably sized protein spacer or linker region that physically displaces the fusion protein away from the cell surface may also be incorporated into the expression vectors. It is possible that in the absence of these spacers the efficiency of protease cleavage may be reduced due to steric hinderance with the cell wall surface. These linker sequences can be incorporated between the protease recognition sequence and the C-terminal sorting signal domain.

Any unique protease cleavage site can be incorporated into the vectors of the present invention. Preferably, the protease cleavage site will be greater than 4 amino acid residues. The most preferred protease for use with the present invention is the TEV NIa proteinase. The TEV NIa proteinase cleaves a specific consensus cleavage site which spans the seven amino acid sequence E-X-V/I/L-Y-X-Q*S/G (X can be any amino acid residue; Doughtery et al., $EMBO\ J.$, 7:1281–1287 (1988)). The preferred cleavage site for the present invention is E-N-L-Y-F-Q*G (Parks et al., $Anal.\ Biochem.$ 216:413–417 (1994)). TEV cleavage sites can be engineered anywhere along the fusion construct; however, the preferred location is immediately adjacent to the proline/glycine rich region harboring the LPXTGX motif (see FIG. 5: RBS=M6 ribosome binding site; ATG=initiation codon; MCS=multiple cloning site (MCS); black bar=membrane spanning domain; closed triangles=engineered cleavage site for TEV (tobacco etch virus) NIa protease; open triangle=cleavage site for factor Xa (IEGR/); small vertical arrow 16=putative cellular signal peptidase cleavage site; see SPEX1b and SPEX1c). The addition of a protein spacer region between the TEV recognition sequence and the glycine/proline-rich anchor region may improve TEV NIa proteinase efficiency. The preferred spacer for the present invention is derived from the M6 protein and contains amino acid residues 222 to 301 (FIG. 5; SPEX1d).

Following protease treatment, the released proteins can be purified in a variety of ways known in the art. Suitable purification method include, but are not limited to, dialysis, ultrafiltration, zonal centrifugation, molecular-exclusion chromatography, isoelectric precipitation, solvent fractionation, electrophoretic separation, thermal precipitation, ion-exchange chromatography, affinity chromatography, and the like. A single step purification using affinity tags is preferred. These affinity tags, like the protease cleavage sites, can be optionally engineered at either the amino or carboxy terminal regions of the fusion protein. Useful affinity tags include, but are not limited to, a polyhistidine tract (HHHHHH), the IgG binding domain of protein A and glutathione S-transferase (GST). Recombinant proteins released from the surface of a gram-positive host can be easily purified in a one step process using metal chelation (e.g., Ni-agarose), protein A-Sepharose, and glutathione-Sepharose column chromatography. N-terminal signal and affinity tag sequences can be easily removed by incorporating a protease cleavage site that is different from the recognition sequence used to remove the protein from the cell surface.

The preferred affinity tag for the present invention is a consecutive stretch of 6 to 10 histidine residues (HHHHHH). A polyhistidine tag of six amino acid residues has been shown to be poorly immunogenic and rarely affects protein function and structure. The polyhistidine affinity tag can be engineered at either the amino or carboxy terminus of the protein. For the present invention, the preferred site is immediately downstream of the N-terminal M6 sequences (FIG. 5).

The N-terminal M6 and affinity tag sequences can be removed from the purified proteins by engineering in a second protease cleavage site. The preferred enzyme for the present invention is factor Xa. The preferred location is immediately downstream of the affinity tag (FIG. 5).

In order to efficiently express the recombinant gene which encodes the fusion protein, regulatory sequences should preferably be included that assure adequate transcription and translation. These vectors should contain transcriptional (i.e., promoters) and translational (i.e., ribosome binding site) control sequences that function in the chosen gram-positive host.

A number of promoters may optionally be used in the practice of the present invention. These regulatory sequences, which are known to those skilled in the art, include heterologous promoters from both gram-negative and gram-positive bacteria. These regulatory sequences can cause the expression of a gene to be turned on or off in response to a chemical or physical stimulus. Alternatively, constitutively expressed promoter elements can also be used.

Gene dosage is a variable that has been shown to possibly have an effect on protein production in several bacterial expression systems. In general, genes present on multiple copy plasmids generate higher levels of protein. The plasmids used for the expression of recombinant proteins in the present invention should be capable of stably replicating in the chosen gram-positive host. These plasmids, which replicate at either a high or low copy number, are familiar to those skilled in the art.

In the present invention, the extrachromosomal elements used in plasmid-linked expression of recombinant genes may optionally contain appropriate genetic markers for selection purposes. Suitable genetic markers include various antibiotic and heavy metal resistance genes as well as nutritional determinants. However, other genes that provide a selective advantage can also be used. Ideally the selective markers should be capable of being expressed in both $E.\ coli$ and gram-positive hosts. This would allow one to carry out the initial cloning in $E.\ coli$ with subsequent transfer of the recombinant plasmid to a gram-positive host. Furthermore, in order to facilitate the insertion of heterologous DNA fragments, plasmids should also contain an in-frame polylinker or MCS which includes useful restriction endonuclease cleavage sites.

Techniques for introducing recombinant plasmids into nontransformable hosts are familiar to those skilled in the art. These methods include, but are not limited to, electroporation (Dower, in $Genetic\ Engineering$-$Principles\ and\ Methods$ Vol. 12, pp. 275–296 (1990)), chemical transformation, conjugation, transduction, and the like. Recombinant DNAs can be easily introduced into those gram-positive species that are naturally competent by transformation.

The presence of certain genes on multiple copy plasmids can occasionally cause toxicity and, in some cases, cell death. The toxic effects of these gene products can many times be reduced by simply decreasing the copy number of the determinant to be expressed. This can be readily achieved by stably integrating the gene encoding the fusion product directly into the host chromosome. The genetic methods that are commonly used to create single copy prokaryotic expression modules involve homologous, site specific and illegitimate (transposition) recombination.

Figure 7:
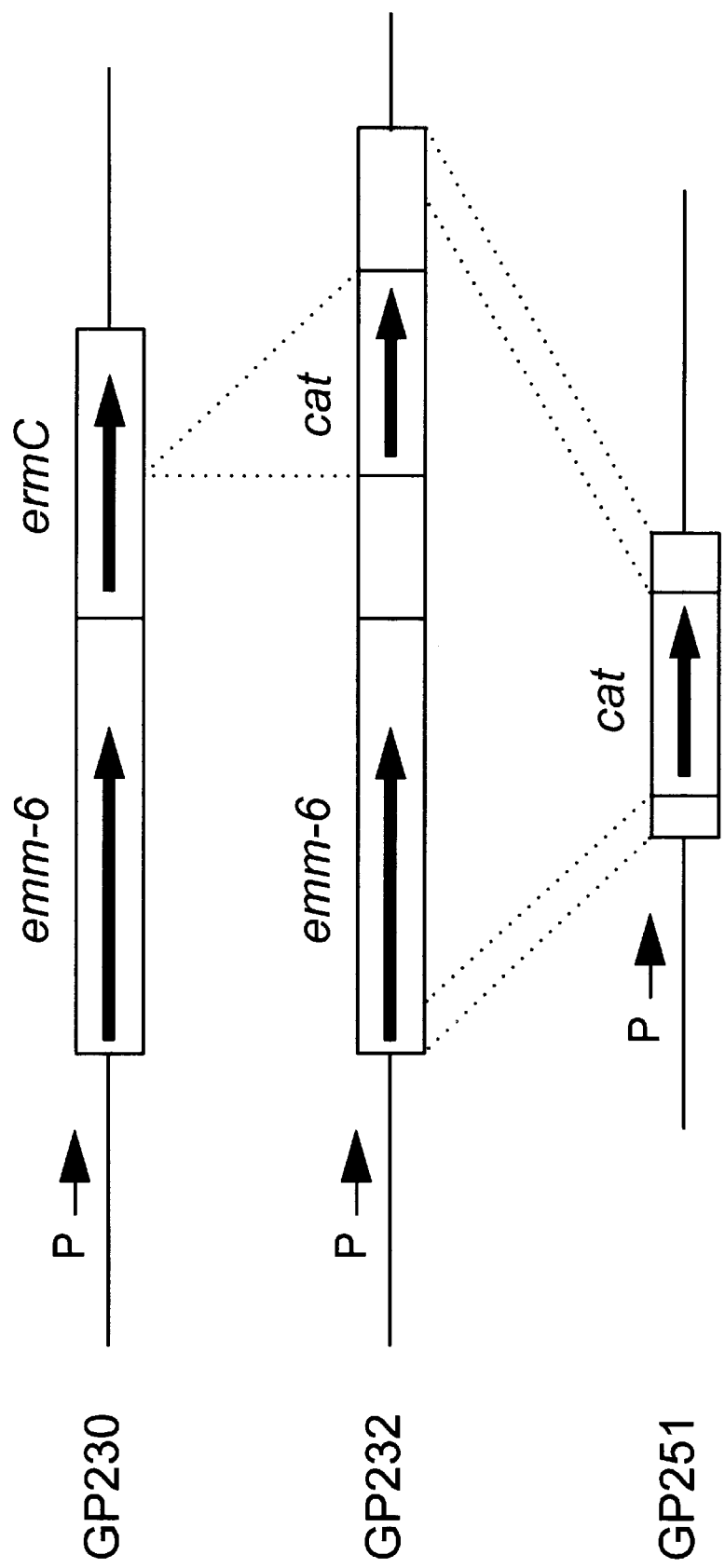
FIG. 7 depicts some possible *S. gordonii* strains for integrated expression of M6 fusion proteins.

The preferred method of gene expression for the present invention involves integration of the recombinant SPEX construct into the S. gordonii chromosome. S. gordonii strains that are useful as expression hosts include GP230 (Pozzi et al., Res. Microbiol. 143:449–457 (1992)), GP232 (Pozzi et al., Infect. Immun., 60:1902–1907 (1992)) and GP251 (Pozzi et al., Vaccine, 12:1071–1077 (1994); FIG. 7: emm-6 is the structural gene for the S. pyogenes type 6M protein. The ermC and cat genes encode erythromycin and chloramphenicol resistance, respectively. Thin lines flanking the inserted (boxed) sequences represents the S. gordonii chromosome. The integrated sequences are located downstream of a strong chromosomal S. gordonii promoter (P)). These strains contain genetic cassettes that have been integrated downstream of a strong S. gordonii promoter via homologous recombination. In the present invention, these cassettes provide flanking regions of homology that will allow one skilled in the art to replace the sequences present on the GP230, GP232 and GP251 with the recombinant SPEX plasmids constructed in vivo.

The following examples are presented in order to more fully illustrate the preferred embodiments of the invention. They should in no way be construed, however, as limiting the broad scope of the invention.

EXAMPLE 1

Construction of SPEX plasmids

A. Anchored vectors

Plasmid pVMB20 (Pozzi et al., Infect. Immun. 60:1902–1907 (1992)) was constructed by subcloning a 3.4 kb ClaI fragment, which contains a promoterless emm-6 gene and a gene encoding erythromycin resistance (ermC; Horinouchi and Weisblum., J. Bacteriol. 150:804–814 (1982)), from pVMB3 (Pozzi et al., Res. Microbiol. 143:449–457 (1992)) into the plasmid pBLUESCRIPT. A 545 bp interior region of the emm-6 gene was removed by KpnI and HinDIII digestion and replaced with a small DNA fragment harboring a synthetic multiple cloning site (MCS). The resulting plasmid, designated pSMB55 (FIG. 4), contains sequences encoding the first 122 N-terminal and the last 140 C-terminal amino acids of the M6 protein. DNA fragments encoding heterologous protein sequences are inserted into the MCS of pSPEX1a or pSPEX2a to form in-frame fusions with the M6 N-terminal and/or C-terminal sequences. The SacI-HpaI fragment from within the ermC determinant of pSMB55 was removed and replaced with a fragment harboring the aphIII gene encoding kanamycin resistance (Trieu-Cuot and Courvalin, Gene, 23:331–341 (1983)). The resulting plasmid was designated pSMB113 (FIG. 4).

Plasmid pSMB104 carries the emm-6$_{A104}$ gene encoding for M6$_{A104}$, a protein containing the first 16 N-terminal and the last 220 C-terminal amino acids (Pozzi, G., unpublished data). The ClaI-KpnI fragment of pSMB104 was used to replace the existing ClaI-KpnI fragment of pSMB113. The resulting plasmid vector, designated pSPEX1a (FIG. 4), can be used to construct protein fusions that contain the N-terminal 58 and C-terminal 140 amino acids of the M6 protein. These protein fusions, when expressed in an appropriate gram-positive host, will be anchored to the bacterial cell surface (FIG. 5).

B. Secretion vectors

Figure 6:
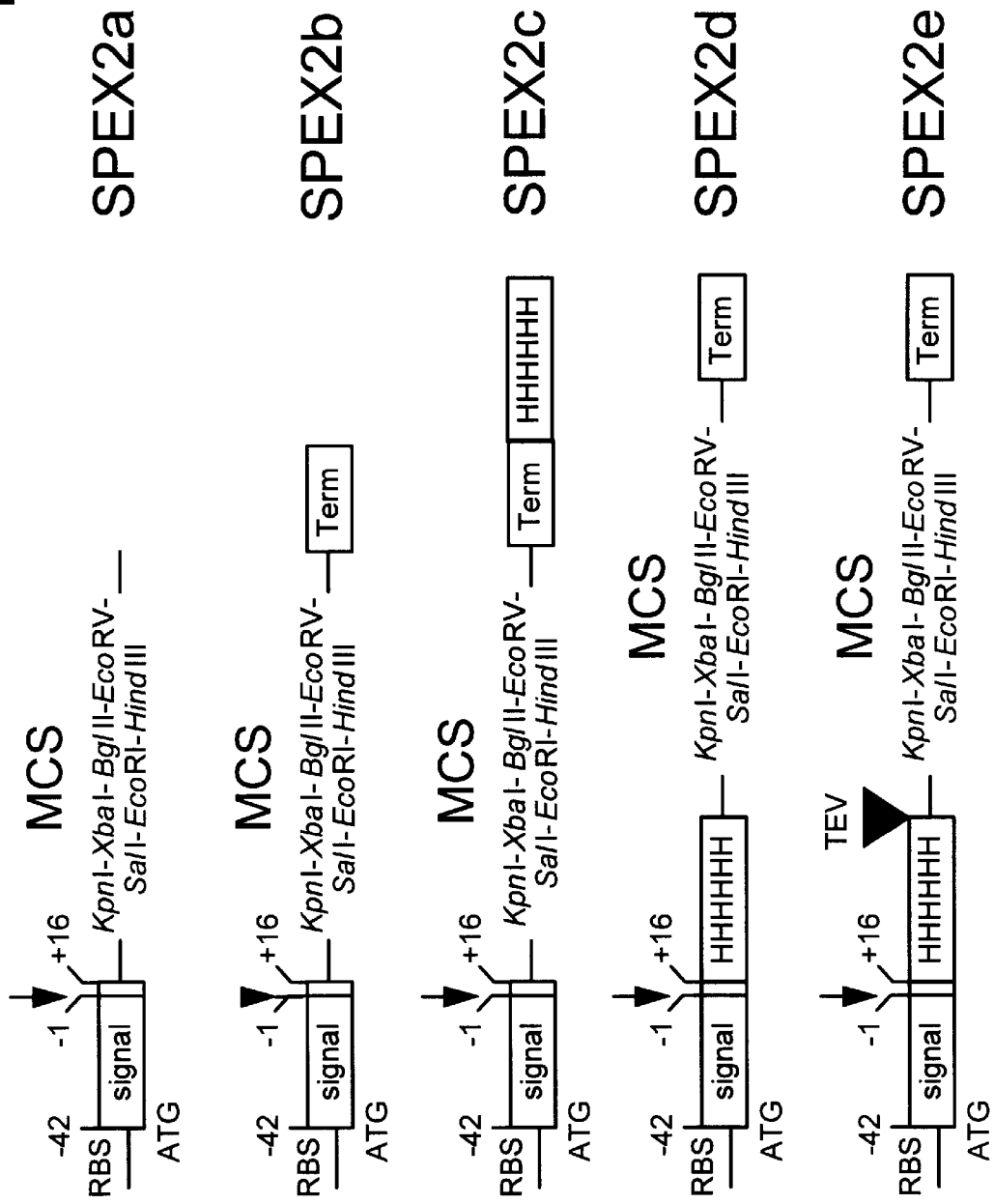
FIG. 6 illustrates possible SPEX cassettes used for the secretion and purification of recombinant proteins.

Deletion of the HinDIII-SacI fragment of pSPEX1a effectively removes the C-terminal sorting signals of the M6 protein. The resulting plasmid, designated pSPEX2a, retains the M6 N-terminal 58 amino acid residues necessary for protein translocation and processing (FIG. 4). As a result, protein fusions generated with pSPEX2a will be secreted into the growth medium. TEV proteinase cleavage sites and polyhistidine tags can be incorporated to facilitate the removal of non-essential protein sequences and for purification purposes, respectively (FIG. 6: RBS=M6 ribosome binding site; ATG=initiation codon; Term=termination codon; triangle=engineered cleavage site for TEV (tobacco etch virus) NIa proteinase; shaded residues=important for proper processing and secretion of M6; small vertical arrow=putative cellular signal peptidase cleavage site).

EXAMPLE 2

Expression of recombinant genes in S. gordonii

In the present invention, recombinant genes encoding M6 fusion proteins can be expressed from multicopy plasmids. Since the preferred expression host in the present invention is S. gordonii, plasmids containing an origin of replication (oriV) that functions in a variety of streptococcal species can be used (Horodniceanu et al., Antimicrob. Agents Chemother., 10:795–801 (1976); Clewell et al., J. Bacteriol., 117:283–289 (1974); Behnke and Ferretti, Plasmid, 4:130–138 (1980); Macrina et al., Infect. Immun. 28:692–699 (1980); Macrina et al., Gene 19:345–353 (1982) ). Alternatively, recombinant genes can be expressed in the form of single copies which have been stably inserted into the S. gordonii chromosome.

Figure 8:
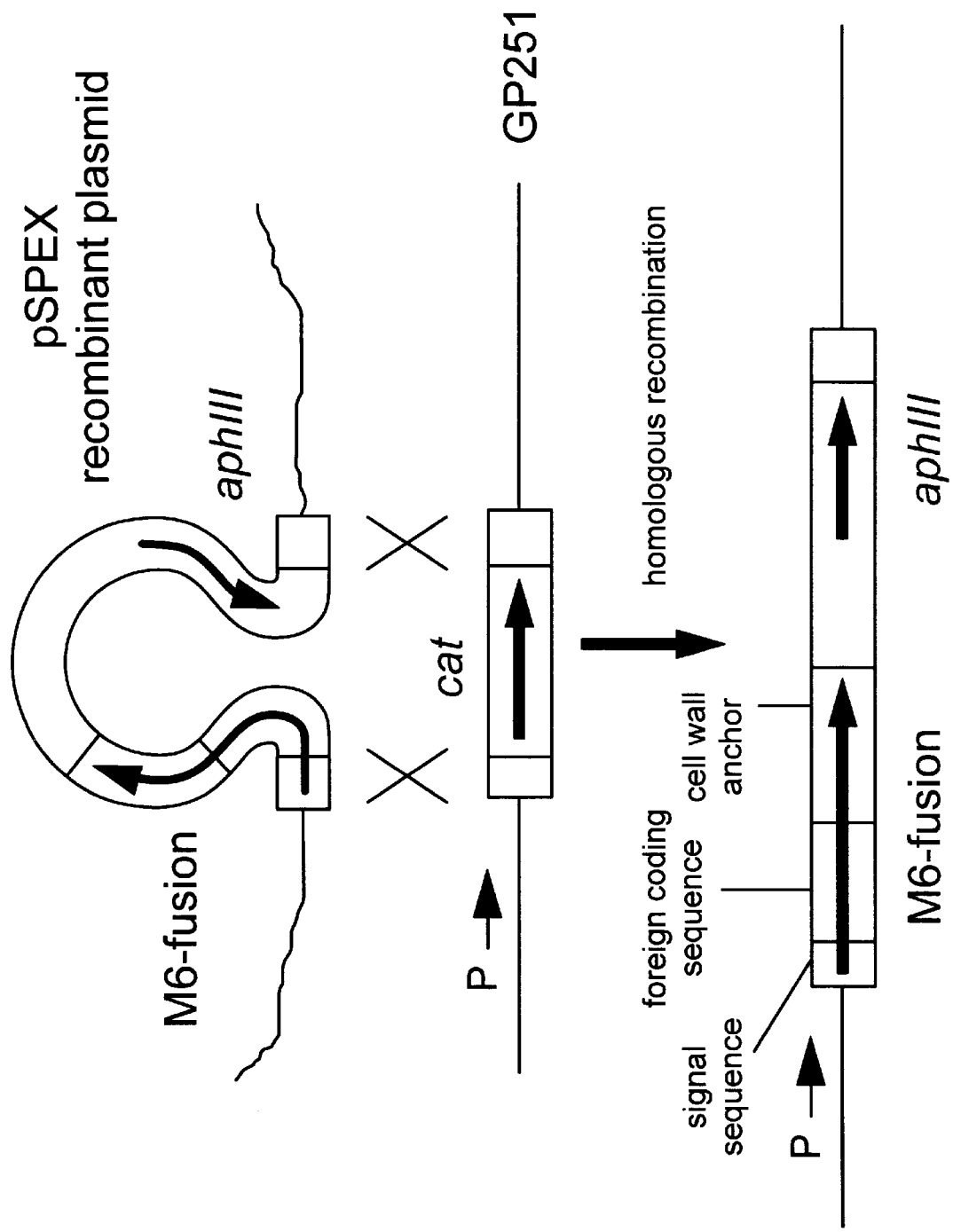
FIG. 8 depicts integration of the M6 fusions into the *S. gordonii* chromosome.

The recombinant plasmid is naturally linearized during transformation (Pozzi et al., Res. Microbiol., 141:659–670 (1990); Pozzi et al., Infect. Immun., 60:1902–1907 (1992)) and recognition of the flanking homologous segments facilitates integration of the M6 gene fusion, together with the aphIII gene (FIG. 8: the cat gene present in the S. gordonii recipient strain GP251 confers chloramphenicol resistance). Recombinant S. gordonii are selected for kanamycin resistance (conferred by aphIII) using the "multilayer" plating technique as previously described by Pozzi et al. (FEMS Microbiol. Lett., 48: 189–194 (1987)). Kanamycin-resistant transformants are then scored for loss of either erythromycin (conferred by ermC) or chloramphenicol (conferred by cat) resistance (depending on the recipient). Antibiotics are used at the following concentrations: erythromycin, 5 µg/ml, chloramphenicol, 5 µg/ml, and kanamycin, 500 µg/ml. Southern blot (Southern, J. Mol. Biol., 98:503 (1975); Southern, Methods Enzymol., 69:152 (1980)) or PCR analysis of purified genomic DNA of Km$^r$(Cm$^s$ or Em$^s$) transformants can be used to establish the structure and copy number of the expression cassette in the bacterial chromosome.

Production of the recombinant protein can be determined by Western blot analysis of whole cell extracts (Towbin et al., Proc. Natl. Acad. Sci. (USA), 76:4350 (1979); Towbin and Gordon, J. Immunol., 72:313 (1984)). Surface expression of the M6 fusion protein can be tested by immunofluorescence according to the procedure described previously (Pozzi et al., Vaccine, 12:1071–1077 (1994)). Recombinant proteins can be detected using polyclonal antisera against the entire M6 molecule, monoclonal antibodies directed against specific M6 epitopes (Jones et al., J. Exp. Med., 164:1226–1238 (1986); Jones and Fischetti, J. Exp. Med., 167:1114–1123 (1988)) or antisera directed against the heterologous protein expressed as a part of the fusion.

EXAMPLE 3

Purification of recombinant proteins from S. gordonii

Recombinant S. gordonii are grown in an appropriate liquid medium such as Todd Hewitt-Yeast Extract Broth (THYEB), brain heart infusion (BHI) or trypticase soy broth (TSB) containing kanamycin at 37° C. for 24 hours or until stationary phase growth is achieved. The bacterial culture is centrifuged and depending on the location of the recombinant protein (cell-wall anchored or secreted) the cell pellet or the spent growth medium is retained for further analysis.

S. gordonii cells harboring surface expressed proteins are collected, washed and resuspended in a minimal volume of PBS (150 mM NaCl, 16 mM $Na_2HPO_4$, 4 mM $NaH_2PO_4$ pH 7.3), in the presence of proteinase inhibitors.

Recombinant proteins with engineered protease cleavage sites are removed from the cell surface by the addition of TEV NIa proteinase. Following incubation for a suitable period of time at 25°–30° C., the cells are removed by centrifugation and the supernatant fluid, which is enriched for the recombinant protein, is collected. Those fusion proteins containing tandem histidine residues can be further purified by passing the supernatant over a nickel-chelating resin (ProBond, Invitrogen Corp.) or nickel nitrilotriacetic acid [Ni-NTA] agarose (Qiagen Inc.). Following washing, the recombinant protein is then eluted from the column using an imidizole gradient under mild conditions (i.e., pH 6.0). The amount of purified protein can be measured by the method of Bradford (Bradford, *Anal. Biochem.*, 72:248–254 (1976)).

The use of the SPEX2 series of vectors (FIG. 6) generates fusion proteins that are secreted into the surrounding medium during growth. Following removal of the bacterial cells, the spent growth medium is retained and used as the starting material for purification of the desired product. Recombinant proteins can be purified using metal chelation chromatography, as described above, and non-essential N-terminal residues can be removed with TEV NIa proteinase treatment.

While the invention has been described and illustrated herein by references to various specific materials, procedures, and examples, it is understood that the invention is not restricted to the particular combinations of materials and procedures selected for that purpose. Numerous variations of such details can be implied and will be appreciated by those skilled in the art.

---

What is claimed is:

1. A method for producing a desired protein in gram-positive bacteria, comprising:

selecting a gram-positive heterologous bacterial host and introducing into the host a plasmid vector comprising DNA fragments encoding amino and carboxy terminal sorting sequences of a gram-positive cell wall surface protein and the desired protein, and transcriptional and translational control sequences that function in the chosen host;

expressing a fusion protein comprising the desired protein, an N-terminal signal sequence, and a C-terminal sorting sequence, wherein the expressed fusion protein is anchored to the host's cell surface;

cleaving the anchored protein from the host's cell surface using a protease; and recovering and purifying the cleaved protein.

2. The method of claim 1 wherein the host is selected from the group consisting of *Aerococcus sp., Bifidobacterium sp., Corprococcus sp., Deinobacter sp., Deinococcus sp., Enterococcus sp., Gemella sp., Lactobacillus sp., Lactococcus sp., Leuconostoc sp., Marinococcus sp., Melissococcus sp., Micrococcus sp, Pediococcus sp., Peptococcus sp., Peptostreptococcus sp., Planococcus sp, Ruminococcus sp., Saccharococcus sp., Salinococcus sp., Carcina sp., Staphylococcus sp., Stomatococcus sp. Streptococcus sp., Trichococcus sp.,* and *Vagococcus sp.*

3. The method of claim 1 wherein the host is from the genus Streptococcus.

4. The method of claim 1 wherein the host is *Streptococcus gordonii*.

5. The method of claim 1 wherein the host is *Streptococcus gordonii* V288 (Challis), GP230, GP232, or GP251.

6. The method of claim 1 wherein the host is deficient in extracellular protease production.

7. The method of claim 1 wherein the gram-positive cell wall surface protein is derived from the genus *Aerococcus, Bifidobacterium, Corprococcus, Deinobacter, Deinococcus, Enterococcus, Gemella, Lactobacillus, Lactococcus, Leuconostoc, Marinococcus, Melissococcus, Micrococcus, Pediococcus, Peptococcus, Peptostreptococcus, Planococcus, Ruminococcus, Saccharococcus, Salinococcus, Carcina, Staphylococcus, Stomatococcus, Streptococcus, Trichococcus,* or *Vagococcus.*

8. The method of claim 7 wherein the gram-positive cell wall surface protein is the type-6 M protein of *Streptococcus pyogenes.*

9. The method of claim 7 wherein the gram-positive cell wall surface protein comprises:

an N-terminal signal sequence comprising a complete leader sequence and a number of amino acid residues from the N-terminus of the mature protein;

a C-terminal sorting signal comprising the LPXTGX motif, wherein X is any amino acid residue, residing within a proline/glycine rich region; a hydrophobic membrane spanning domain; and a charged tail.

10. The method of claim 9, wherein the gene encoding the gram-positive cell wall surface protein additionally comprises a DNA fragment encoding a recognition sequence for at least one restriction endonuclease (the multiple cloning site, MCS) located between the DNA sequences that encode the amino- and carboxy-terminal sorting signals.

11. The method of claim 7 wherein the plasmid vector comprises sequences coding for the M6 ribosome binding site, the translation initiation codon (ATG), the 42 amino acid leader sequence (−42 to −1), and a portion of the mature N-terminus which is at least 5 amino acids long.

12. The method of claim 11 wherein the portion of the N-terminus coded for comprises residues −42 to +16.

13. The method of claim 1 wherein the plasmid vector further encodes at least one cleavage site for a proteolytic enzyme.

14. The method of claim 1 wherein the protease is the proteinase of tobacco etch virus (TEV), thrombin, enterokinase, or factor Xa.

15. The method of claim 1 wherein the cleaved proteins are purified using metal chelation, protein A-Sepharose, glutathione-Sepharose column chromatography, or a combination thereof.

16. The method of claim 1 wherein the plasmid vector additionally comprises extrachromosomal genetic markers that are sufficient to provide a selective advantage to a host expressing said genetic markers.

17. The method of claim 16 wherein the genetic markers are antibiotic genes, heavy metal resistance genes, and nutritional determinants.

18. The method of claim 16 wherein the plasmid vector additionally comprises a polylinker or multiple cloning site which includes restriction endonuclease cleavage sites.

19. The method of claim 1 wherein the C-terminal sorting signal is derived from the M protein of type-6 *S. pyogenes.*

20. The method of claim 1 wherein the plasmid vector additionally encodes the M6 C-terminal residues 302 to 441, termination codon (TAA), and downstream sequences which comprise a transcriptional terminator.

21. The method of claim 1, wherein the pSPEX1a vector additionally encodes a protease which recognizes a cleavage site of greater than 4 amino acid residues.

22. The method of claim 1, wherein the protease is the TEV NIa proteinase, which cleaves a specific consensus cleavage site which spans the seven amino acid sequence E-X-V/I/L-Y-X-Q*S/G, wherein X can be any amino acid residue.

23. The method of claim 22, wherein the cleavage site is E-N-L-Y-F-Q*G.

24. The method of claim 22, wherein the cleavage site is located adjacent to the proline/glycine-rich region harboring the LPXTGX motif.

25. The method of claim 22, wherein a protein spacer is added between the TEV proteinase recognition sequence and the proline/glycine-rich anchor region.

26. The method of claim 25, wherein the spacer is derived from the M6 protein and consists of amino acid residues 222 to 301.

27. A method for producing a desired protein in gram-positive bacteria, comprising:

selecting a gram-positive, heterologous bacterial host and introducing into the host a plasmid vector comprising DNA fragments encoding amino and carboxy terminal sorting sequences of a gram-positive cell wall surface protein and the desired protein, and transcriptional and translational control sequences that function in the chosen host;

expressing a fusion protein comprising the desired protein, an N-terminal signal sequence, and a C-terminal sorting sequence wherein the expressed fusion protein is anchored to the host's cell surface;

cleaving the anchored protein from the host's cell surface using a protease; and recovering and purifying the cleaved protein; wherein the plasmid vector is pSPEX1a.

28. The method of claim 27 wherein the cleaved proteins are purified in a single step through the use of affinity tags.

29. The method of claim 28 wherein the affinity tags are polyhistidine tracts containing from 6 to 10 histidine residues, the IgG binding domain of protein A, or glutathione S-transferase.

30. A method for expressing a desired protein in gram-positive bacteria, comprising:

selecting a heterologous, gram-positive bacterial host;
introducing into the host a plasmid vector comprising
   DNA fragments encoding amino terminal sorting sequences of a gram-positive cell wall surface protein, and the desired protein; and
   transcriptional and translational control sequences that function in the chosen host;
expressing a fusion protein comprising
   the desired protein, and
   an N-terminal signal sequence wherein the expressed protein is secreted from the cell; and
   purifying the protein product from the supernatant fluid following secretion;
wherein the plasmid vector is one of the SPEX2 series of vectors.

31. The method of claim 30 wherein the host is selected from the genus *Aerococcus, Bifidobacterium, Corprococcus, Deinobacter, Deinococcus, Enterococcus, Gemella, Lactobacillus, Lactococcus, Leuconostoc, Marinococcus, Melissococcus, Micrococcus, Pediococcus, Peptococcus, Peptostreptococcus, Planococcus, Ruminococcus, Saccharococcus, Salinococcus, Carcina, Staphylococcus, Stomatococcus, Streptococcus, Trichococcus,* or *Vagococcus.*

32. The method of claim 30 wherein the host is from the genus Streptococcus.

33. The method of claim 30, wherein the host is *Streptococcus gordonii*.

34. The method of claim 30, wherein the host is *Streptococcus gordonii* V288 (Challis), GP230, GP232, or GP251.

35. The method of claim 30 wherein the host is deficient in extracellular protease production.

36. The method of claim 30 wherein the gram-positive cell wall surface protein comprises:
   an N-terminal signal sequence comprising a complete leader sequence and a number of amino acid residues from the N-terminus of the mature protein;
   a hydrophobic membrane spanning domain; and
   a charged tail.

37. The method of claim 36, wherein the plasmid vector additionally encodes a recognition sequence for at least one restriction endonuclease (the multiple cloning site, MCS) operably linked to the DNA sequences that encode the amino-terminal sorting signals.

38. The method of claim 30 wherein the plasmid vector additionally encodes extrachromosomal genetic markers that are sufficient to provide a selective advantage to a host expressing said genetic markers.

39. The method of claim 38 wherein the genetic markers are antibiotic genes, heavy metal resistance genes, and nutritional determinants.

40. The method of claim 38 wherein the genetic markers are expressed in both *E. coli* and gram-positive hosts.

41. The method of claim 38 wherein the plasmid vector additionally encodes a polylinker or multiple cloning site containing restriction endonuclease cleavage sites.

42. The method of claim 30 wherein the plasmid vector comprises sequences coding for the M6 ribosome binding site, the translation initiation codon (ATG), the 42 amino acid leader sequence (−42 to −1), and a portion of the mature N-terminus which is at least 5 amino acids long.

43. The method of claim 30 wherein the plasmid vector comprises sequences coding for the M6 ribosome binding site, the translation initiation codon (ATG), the 42 amino acid leader sequence (−42 to −1), and a portion of the mature N-terminus which is at least 5 amino acids long.

44. The method of claim 30 wherein recombinant proteins are purified using metal chelation chromatography.

45. The method of claim 30 wherein non-essential N-terminal residues can be removed with TEV NIa proteinase treatment.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 43 amino acids
        ( B ) TYPE: amino acid
        ( C ) STRANDEDNESS: Not Relevant
        ( D ) TOPOLOGY: Not Relevant ( i i ) MOLECULE TYPE: peptide ( v ) FRAGMENT TYPE: C-terminal ( v i ) ORIGINAL SOURCE:
        ( A ) ORGANISM: Staphylococcus aureus
        ( B ) STRAIN: Protein A ( x i ) SEQUENCE DESCRIPTION: SEQ ID NO:1:

```
Ala  Asp  Ala  Asn  Lys  Ala  Gln  Ala  Leu  Pro  Glu  Thr  Gly  Glu  Glu  Asn
1                   5                        10                       15

Pro  Leu  Ile  Gly  Thr  Thr  Val  Phe  Gly  Gly  Leu  Ser  Leu  Ala  Leu  Gly
               20                       25                       30

Ala  Ala  Leu  Leu  Ala  Gly  Arg  Arg  Arg  Glu  Leu
               35                       40
```

( 2 ) INFORMATION FOR SEQ ID NO:2:

( i ) SEQUENCE CHARACTERISTICS:
        ( A ) LENGTH: 43 amino acids
        ( B ) TYPE: amino acid
        ( C ) STRANDEDNESS: Not Relevant
        ( D ) TOPOLOGY: Not Relevant ( i i ) MOLECULE TYPE: peptide ( v ) FRAGMENT TYPE: C-terminal ( v i ) ORIGINAL SOURCE:
        ( A ) ORGANISM: Streptococcus pyogenes (B) STRAIN: M6 protein (x i) SEQUENCE DESCRIPTION: SEQ ID NO:2:

```
Pro Met Lys Glu Thr Lys Arg Gln Leu Pro Ser Thr Gly Glu Thr Ala
1               5                   10                  15
Asn Pro Phe Phe Thr Ala Ala Ala Leu Thr Val Met Ala Thr Ala Gly
                20                  25                  30
Val Ala Ala Val Val Lys Arg Lys Glu Glu Asn
                35                  40
```

(2) INFORMATION FOR SEQ ID NO:3:

(i) SEQUENCE CHARACTERISTICS:
        (A) LENGTH: 40 amino acids
        (B) TYPE: amino acid
        (C) STRANDEDNESS: Not Relevant
        (D) TOPOLOGY: Not Relevant (i i) MOLECULE TYPE: peptide (v) FRAGMENT TYPE: C-terminal (v i) ORIGINAL SOURCE:
        (A) ORGANISM: S. mutans
        (B) STRAIN: WapA (x i) SEQUENCE DESCRIPTION: SEQ ID NO:3:

```
Thr Lys Gln Lys Ala Lys Phe Val Leu Pro Ser Thr Gly Glu Gln Ala
1               5                   10                  15
Gly Leu Leu Leu Thr Thr Val Gly Leu Val Ile Val Ala Val Ala Gly
                20                  25                  30
Val Tyr Phe Tyr Arg Thr Arg Arg
                35                  40
```

(2) INFORMATION FOR SEQ ID NO:4:

(i) SEQUENCE CHARACTERISTICS:
        (A) LENGTH: 42 amino acids
        (B) TYPE: amino acid
        (C) STRANDEDNESS: Not Relevant
        (D) TOPOLOGY: Not Relevant (i i) MOLECULE TYPE: peptide (v) FRAGMENT TYPE: C-terminal (v i) ORIGINAL SOURCE:
        (A) ORGANISM: Streptococcus pyogenes
        (B) STRAIN: M49 protein (x i) SEQUENCE DESCRIPTION: SEQ ID NO:4:

```
Ala Met Thr Gln Gln Lys Arg Thr Leu Pro Ser Thr Gly Glu Thr Ala
1               5                   10                  15
Asn Pro Phe Phe Thr Ala Ala Ala Ala Thr Val Met Val Ser Ala Gly
                20                  25                  30
Met Leu Ala Leu Lys Arg Lys Glu Glu Asn
                35                  40
```

(2) INFORMATION FOR SEQ ID NO:5:

(i) SEQUENCE CHARACTERISTICS:
        (A) LENGTH: 23 amino acids
        (B) TYPE: amino acid
        (C) STRANDEDNESS: Not Relevant
        (D) TOPOLOGY: Not Relevant (i i) MOLECULE TYPE: peptide (v) FRAGMENT TYPE: C-terminal (vi) ORIGINAL SOURCE:
(B) STRAIN: streptococcal IgA- binding protein (xi) SEQUENCE DESCRIPTION: SEQ ID NO:5:

Pro Met Ala Gln Thr Lys Arg Gln Leu Pro Ser Thr Gly Glu Glu Thr
1               5                   10                  15

Thr Asn Pro Phe Phe Thr Ala
            20

(2) INFORMATION FOR SEQ ID NO:6:

(i) SEQUENCE CHARACTERISTICS:
(A) LENGTH: 43 amino acids
(B) TYPE: amino acid
(C) STRANDEDNESS: Not Relevant
(D) TOPOLOGY: Not Relevant (ii) MOLECULE TYPE: peptide (v) FRAGMENT TYPE: C-terminal (vi) ORIGINAL SOURCE:
(B) STRAIN: streptococcal protein G (xi) SEQUENCE DESCRIPTION: SEQ ID NO:6:

Asp Asp Ala Lys Lys Ala Glu Thr Leu Pro Thr Thr Gly Glu Gly Ser
1               5                   10                  15

Asn Pro Phe Phe Thr Ala Ala Ala Leu Ala Val Met Ala Gly Ala Gly
            20                  25                  30

Ala Leu Ala Val Ala Ser Lys Arg Lys Glu Asp
            35                  40

(2) INFORMATION FOR SEQ ID NO:7:

(i) SEQUENCE CHARACTERISTICS:
(A) LENGTH: 45 amino acids
(B) TYPE: amino acid
(C) STRANDEDNESS: Not Relevant
(D) TOPOLOGY: Not Relevant (ii) MOLECULE TYPE: peptide (v) FRAGMENT TYPE: C-terminal (vi) ORIGINAL SOURCE:
(B) STRAIN: staphylococcal fibronectin-binding protein (xi) SEQUENCE DESCRIPTION: SEQ ID NO:7:

Lys Pro Gln Ser Lys Lys Ser Glu Leu Pro Glu Thr Gly Gly Glu Glu
1               5                   10                  15

Ser Thr Asn Lys Gly Met Leu Phe Gly Gly Leu Phe Ser Ile Leu Gly
            20                  25                  30

Leu Ala Leu Leu Arg Arg Asn Lys Lys Asn His Lys Ala
            35                  40                  45

(2) INFORMATION FOR SEQ ID NO:8:

(i) SEQUENCE CHARACTERISTICS:
(A) LENGTH: 42 amino acids
(B) TYPE: amino acid
(C) STRANDEDNESS: Not Relevant
(D) TOPOLOGY: Not Relevant (ii) MOLECULE TYPE: peptide (v) FRAGMENT TYPE: C-terminal (v i) ORIGINAL SOURCE:
  (B) STRAIN: streptococcal T6 protein (x i) SEQUENCE DESCRIPTION: SEQ ID NO:8:

```
Ile Pro Asn Thr Lys Leu Gly Glu Leu Pro Ser Thr Gly Ser Ile Gly
1               5                   10                  15
Thr Tyr Leu Phe Lys Ala Ile Gly Ser Ala Ala Met Ile Gly Ala Ile
                20                  25                  30
Gly Ile Tyr Ile Val Lys Arg Arg Lys Ala
            35                  40
```

(2) INFORMATION FOR SEQ ID NO:9:

(i) SEQUENCE CHARACTERISTICS:
    (A) LENGTH: 42 amino acids
    (B) TYPE: amino acid
    (C) STRANDEDNESS: Not Relevant
    (D) TOPOLOGY: Not Relevant (i i) MOLECULE TYPE: peptide (v) FRAGMENT TYPE: C-terminal (v i) ORIGINAL SOURCE:
    (A) ORGANISM: S. mutans
    (B) STRAIN: Pac (x i) SEQUENCE DESCRIPTION: SEQ ID NO:9:

```
Gln Pro Ser Ser Val Gln Glu Thr Leu Pro Asn Thr Gly Val Thr Asn
1               5                   10                  15
Asn Ala Tyr Met Pro Leu Leu Gly Ile Ile Gly Leu Val Thr Ser Phe
                20                  25                  30
Ser Leu Leu Gly Leu Lys Ala Lys Lys Asp
            35                  40
```

(2) INFORMATION FOR SEQ ID NO:10:

(i) SEQUENCE CHARACTERISTICS:
    (A) LENGTH: 44 amino acids
    (B) TYPE: amino acid
    (C) STRANDEDNESS: Not Relevant
    (D) TOPOLOGY: Not Relevant (i i) MOLECULE TYPE: peptide (v) FRAGMENT TYPE: C-terminal (v i) ORIGINAL SOURCE:
    (A) ORGANISM: S. cremoris
    (B) STRAIN: Wg2 (surface protease)

(x i) SEQUENCE DESCRIPTION: SEQ ID NO:10:

```
Gln Leu Thr Ser Gly Lys Gly Ala Leu Pro Lys Thr Gly Glu Thr Thr
1               5                   10                  15
Glu Arg Pro Ala Phe Gly Phe Leu Gly Val Ile Val Val Ile Leu Met
                20                  25                  30
Gly Val Leu Gly Leu Lys Arg Lys Gln Arg Glu Glu
            35                  40
```

(2) INFORMATION FOR SEQ ID NO:11:

(i) SEQUENCE CHARACTERISTICS:
    (A) LENGTH: 6 amino acids
    (B) TYPE: amino acid
    (C) STRANDEDNESS: Not Relevant
    (D) TOPOLOGY: Not Relevant (i i) MOLECULE TYPE: peptide (v) FRAGMENT TYPE: internal (ix) FEATURE:
    (A) NAME/KEY: Region
    (B) LOCATION: 1..6
    (D) OTHER INFORMATION: /note= "consensus sequence"

(xi) SEQUENCE DESCRIPTION: SEQ ID NO:11:

```
Leu  Pro  Xaa  Thr  Gly  Xaa
1                  5
```

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: internal (ix) FEATURE:
        (A) NAME/KEY: Region
        (B) LOCATION: 1..6
        (D) OTHER INFORMATION: /note= "consensus region of SEQ ID NO:1"

(xi) SEQUENCE DESCRIPTION: SEQ ID NO:12:

```
Leu  Pro  Glu  Thr  Gly  Glu
1                  5
```

(2) INFORMATION FOR SEQ ID NO:13:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (v) FRAGMENT TYPE: C-terminal (ix) FEATURE:
        (A) NAME/KEY: Region
        (B) LOCATION: 1..6
        (D) OTHER INFORMATION: /note= "charged-tail"

(xi) SEQUENCE DESCRIPTION: SEQ ID NO:13:

```
Lys  Arg  Lys  Glu  Glu  Asn
1                  5
```

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:14:

```
His  His  His  His  His  His
1                  5
```